US012622739B2

(12) United States Patent
Kadowaki et al.

(10) Patent No.: US 12,622,739 B2
(45) Date of Patent: May 12, 2026

(54) ELECTRODE WITH CONDUIT AND TREATMENT TOOL

(71) Applicant: OLYMPUS CORPORATION, Hachioji (JP)

(72) Inventors: Tsubasa Kadowaki, Hachioji (JP); Ryu Yorita, Hachioji (JP); Ojiro Kitamura, Hachioji (JP); Yohei Motoki, Fuchu (JP); Sho Ogawa, Hachioji (JP); Tadashi Kitayama, Sagamihara (JP); Naoki Otaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 741 days.

(21) Appl. No.: 17/684,588

(22) Filed: Mar. 2, 2022

(65) Prior Publication Data

US 2022/0183742 A1     Jun. 16, 2022

Related U.S. Application Data

(63) Continuation of application No. PCT/JP2020/035324, filed on Sep. 17, 2020.
(Continued)

(51) Int. Cl.
*A61B 18/14* (2006.01)
*A61B 18/00* (2006.01)

(52) U.S. Cl.
CPC .... *A61B 18/14* (2013.01); *A61B 2018/00083* (2013.01); *A61B 2018/00589* (2013.01); *A61B 2018/1405* (2013.01)

(58) Field of Classification Search
CPC ............... A61B 18/14; A61B 18/1482; A61B 2018/00083; A61B 2018/00589;
(Continued)

(56) References Cited

U.S. PATENT DOCUMENTS 6,176,857 B1     1/2001   Ashley
6,210,405 B1     4/2001   Goble et al.
(Continued)

FOREIGN PATENT DOCUMENTS

JP     2000-512526 A     9/2000
JP     2003-116870 A     4/2003
(Continued)

OTHER PUBLICATIONS

Dec. 1, 2020 International Search Report issued in International Patent Application No. PCT/JP2020/035324.

*Primary Examiner* — Tigist S Demie

(74) *Attorney, Agent, or Firm* — Oliff PLC

(57) ABSTRACT

An electrode with a conduit includes: a tubular portion internally provided with a first conduit; a distal end portion provided at the distal end of the tubular portion; a second conduit that is provided inside the distal end portion, the second conduit being configured to communicate with the first conduit; an opening configured to communicate with the first conduit and the second conduit; a first hemostatic surface that has a flat surface extending from the distal end of the tubular portion in an extending direction of the second conduit, and serves as an electrode configured to cause a high-frequency current to flow through a biological tissue; and a second hemostatic surface that is connected to a distal end side of the first hemostatic surface and is provided at an end portion protruding toward a distal end side from the opening.

22 Claims, 11 Drawing Sheets

Related U.S. Application Data

(60) Provisional application No. 62/905,711, filed on Sep. 25, 2019.

(58) Field of Classification Search
CPC ........... A61B 2018/00744; A61B 2018/00863; A61B 2018/1405; A61B 2218/002; A61B 2218/007
See application file for complete search history.

(56) References Cited

U.S. PATENT DOCUMENTS

| | | | | | |
|---|---|---|---|---|---|
| 2003/0023239 | A1* | 1/2003 | Burbank | ............ | A61B 18/1482 606/171 |
| 2005/0049454 | A1 | 3/2005 | Ouchi | | |
| 2006/0293653 | A1* | 12/2006 | Van Wyk | ........... | A61B 18/1485 606/49 |
| 2012/0330292 | A1* | 12/2012 | Shadduck | ........ | A61B 17/32002 606/29 |
| 2014/0100557 | A1* | 4/2014 | Bohner | .............. | A61B 18/1485 606/46 |
| 2015/0105777 | A1* | 4/2015 | Benn | .................... | A61B 18/148 606/47 |
| 2015/0374431 | A1 | 12/2015 | Davies et al. | | |
| 2019/0192175 | A1 | 6/2019 | Chida et al. | | |

FOREIGN PATENT DOCUMENTS

| | | |
|---|---|---|
| JP | 2005-066139 A | 3/2005 |
| JP | 3148843 U | 2/2009 |
| JP | 2015-083127 A | 4/2015 |
| JP | 2017-506986 A | 3/2017 |
| JP | 2020-005875 A | 1/2020 |
| WO | 1997/048346 A1 | 12/1997 |
| WO | 2015/136338 A1 | 9/2015 |
| WO | 2018/043279 A1 | 3/2018 |

* cited by examiner

ELECTRODE WITH CONDUIT AND TREATMENT TOOL

CROSS-REFERENCE TO RELATED APPLICATIONS

This application is a continuation of PCT international application Ser. No. PCT/JP2020/035324 filed on Sep. 17, 2020 which designates the United States, incorporated herein by reference, and which claims the benefit of priority from U.S. Patent Applications No. 62/905,711, filed on Sep. 25, 2019, incorporated herein by reference.

BACKGROUND

1. Technical Field

The present disclosure relates to an electrode with a conduit and a treatment tool.

2. Related Art

In the related art, a treatment tool has been introduced, which has a suction function of sucking up body fluid or the like, and a hemostatic function of causing a high-frequency current to flow through a hemostasis target site in a biological tissue in order to stop bleeding (see, for example, JP 2020-5875 A).

A treatment tool (surgical suction tube having a coagulation function) described in JP 2020-5875 A includes a tube member having a hollow hole and an electrode that causes a high-frequency current to flow to a hemostasis target site. The electrode has a bottomed cylindrical shape, and is attached to an end portion of the tubular member in a posture of closing the end portion. In addition, a side surface of the electrode is provided with an opening communicating the inside of the electrode (inside of the tubular member) and the outside of the electrode, which is designed to suction body fluid or the like.

SUMMARY

In exemplary embodiments, an electrode with a conduit includes: a tubular portion internally provided with a first conduit extending along a longitudinal axis connecting a distal end and a proximal end of the tubular portion; a distal end portion provided at the distal end of the tubular portion; a second conduit that is provided inside the distal end portion and that extends in a direction intersecting the longitudinal axis, the second conduit being configured to communicate with the first conduit; an opening configured to open in a direction intersecting the longitudinal axis and communicate with the first conduit and the second conduit; a first hemostatic surface that constitutes a part of an outer surface of the distal end portion, has a flat surface extending from the distal end of the tubular portion in an extending direction of the second conduit, and serves as an electrode configured to cause a high-frequency current to flow through a biological tissue; and a second hemostatic surface that is connected to a distal end side of the first hemostatic surface and is provided at an end portion protruding toward a distal end side from the opening.

In exemplary embodiments, a treatment tool includes: a tubular sheath; and an electrode with a conduit, the electrode being provided at a distal end of the sheath. The electrode with the conduit includes: a tubular portion internally provided with a first conduit extending along a longitudinal axis connecting a distal end and a proximal end of the tubular portion, the first conduit being configured to communicate with an inside of the sheath; and a distal end portion provided at the distal end of the tubular portion, and the distal end portion includes: a second conduit that is provided inside the distal end portion and that extends in a direction intersecting the longitudinal axis, the second conduit being configured to communicate with the first conduit; an opening that is provided at a distal end of the second conduit, the opening being configured to allow communication between the second conduit and an outside of the distal end portion and open in a direction intersecting the longitudinal axis; and a first hemostatic surface that constitutes a part of an outer surface of the distal end portion and that serves as an electrode configured to apply high-frequency energy to a biological tissue.

The above and other features, advantages and technical and industrial significance of this disclosure will be better understood by reading the following detailed description of presently exemplary embodiments of the disclosure, when considered in connection with the accompanying drawings.

DETAILED DESCRIPTION

Figure 1:
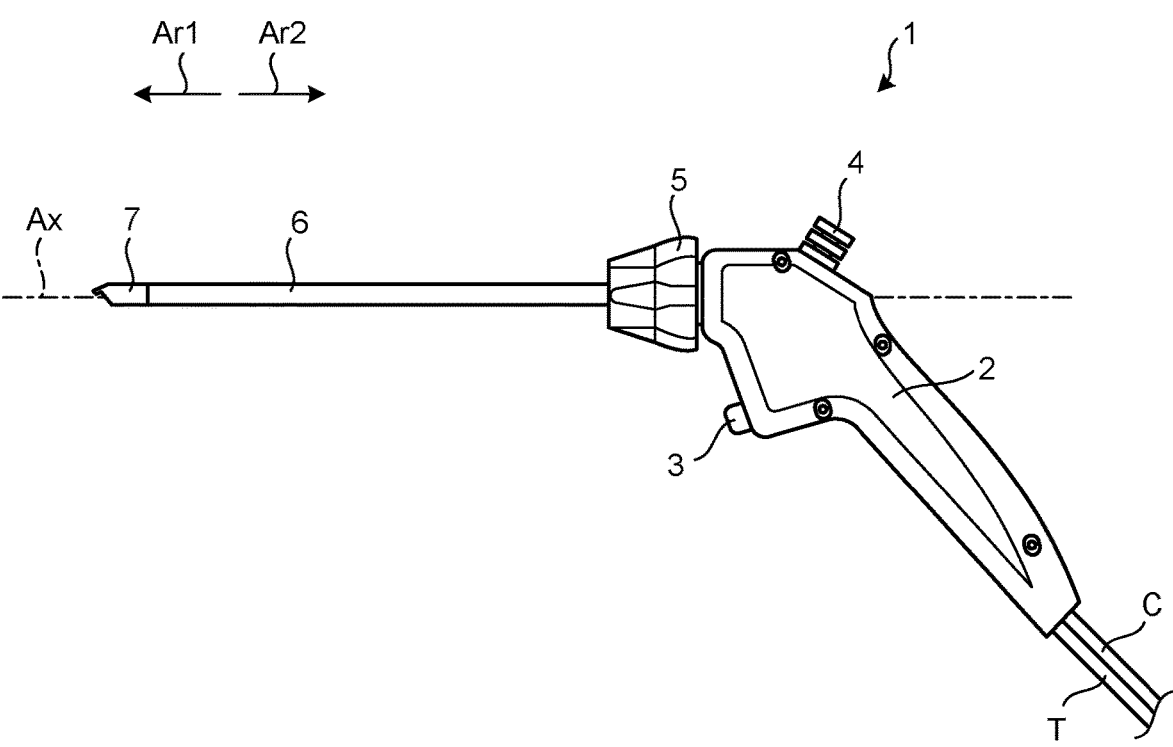
FIG. 1 is a view illustrating a treatment tool according to an exemplary embodiment.

Hereinafter, the modes for carrying out the disclosure (hereinafter "embodiment(s)") will be described with reference to the drawings. However, the disclosure is not limited to the embodiments described below. Furthermore, the same components are denoted by the same reference numerals in the description of the drawings.

Schematic Configuration of Treatment Tool

FIG. 1 is a view illustrating a treatment tool 1 according to an exemplary embodiment.

The treatment tool 1 is a treatment tool having a suction function of sucking up body fluid or the like, and a hemostatic function of causing a high-frequency current to flow through a hemostasis target site in a biological tissue in order to stop bleeding. As illustrated in FIG. 1, the treatment tool 1 includes a housing 2, a hemostasis initiating switch 3, a suction switch (not illustrated), a water supply switch 4, a rotary knob 5, a sheath 6, and a conduit electrode 7 (electrode with a conduit).

Hereinafter, one side along a central axis Ax of the sheath 6 is referred to as a distal end side Ar1, and the other side is referred to as a proximal end side Ar2. The central axis Ax corresponds to a longitudinal axis.

The housing 2 is a portion that supports the entire treatment tool 1 and is held by an operator's hand.

The hemostasis initiating switch 3 is provided in a state of being exposed to the outside of the housing 2, and is a portion that receives a hemostasis initiating operation by the operator. The hemostasis initiating operation is an operation for stopping bleeding at a hemostasis target site.

Although not specifically illustrated, the suction switch is provided in a state of being exposed to the outside of the housing 2, and is a portion that receives a suction operation by the operator. The suction operation is an operation for sucking up body fluid, water, and the like, stored in the hemostasis target site.

The water supply switch 4 is provided in a state of being exposed to the outside of the housing 2, and is a portion that receives a water supply operation by the operator. The water supply operation is an operation for supplying a fluid (hereinafter referred to as "water") such as physiological saline to the hemostasis target site.

The rotary knob 5 has a substantially cylindrical shape coaxial with the central axis Ax, and is provided at the distal end side Ar1 of the housing 2. The rotary knob 5 receives a rotating operation by the operator. The rotating operation is an operation for rotating the sheath 6 and the conduit electrode 7 about the central axis Ax. The rotary knob 5, the sheath 6, and the conduit electrode 7 rotate about the central axis Ax by the rotating operation.

The sheath 6 is a cylindrical pipe made of a conductive material such as metal. Ar1 end portion of the sheath 6 on the proximal end side Ar2 is supported by the housing 2 while being inserted into the rotary knob 5. Although not specifically illustrated, an outer surface of the sheath 6 is covered with a tube having electrical insulation property.

The conduit electrode 7 is made of a conductive material such as metal, and is provided at an end portion of the sheath 6 on the distal end side Ar1.

A detailed configuration of the conduit electrode 7 will be described hereinbelow.

Configuration of Conduit Electrode

Figure 2:
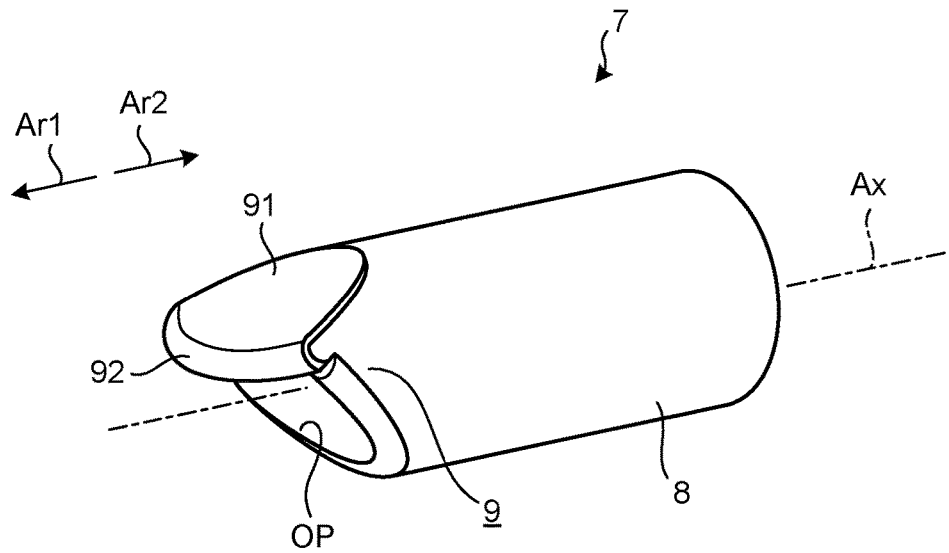
FIG. 2 is a view illustrating an electrode with a conduit.
Figure 3:
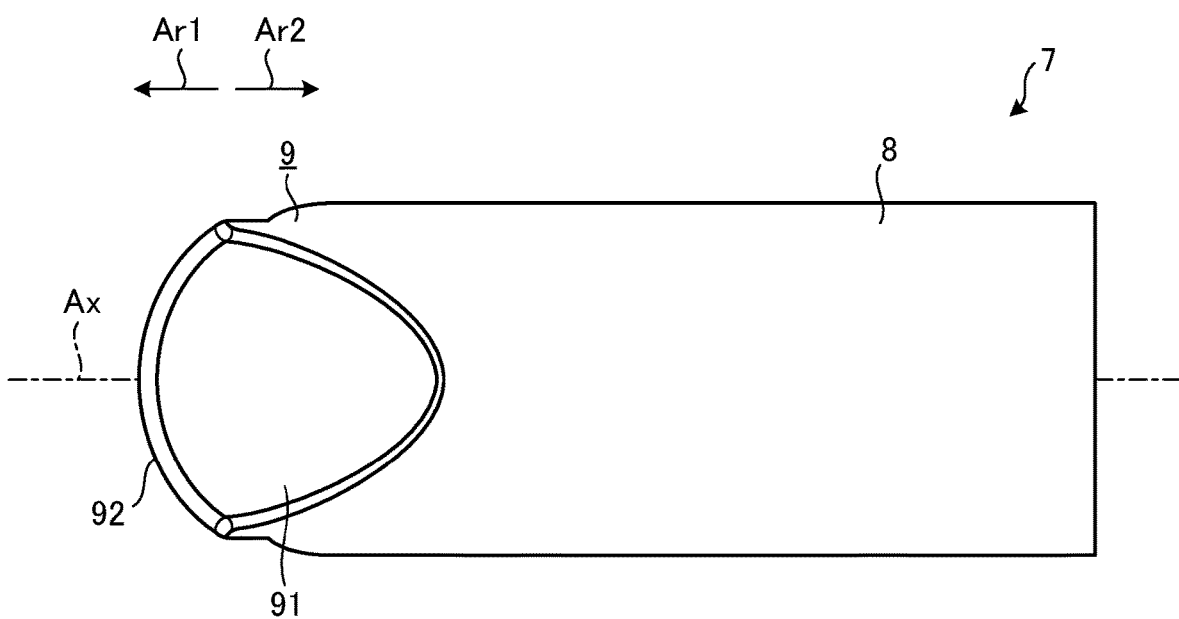
FIG. 3 is a view illustrating an electrode with a conduit.
Figure 4:
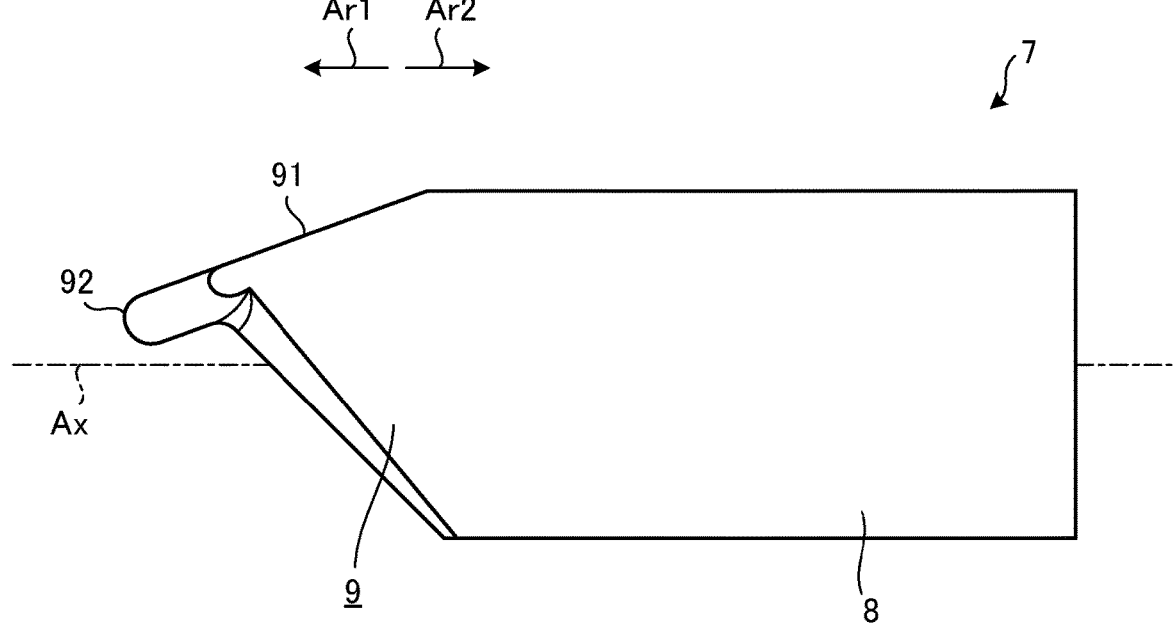
FIG. 4 is a view illustrating an electrode with a conduit.
Figure 5:
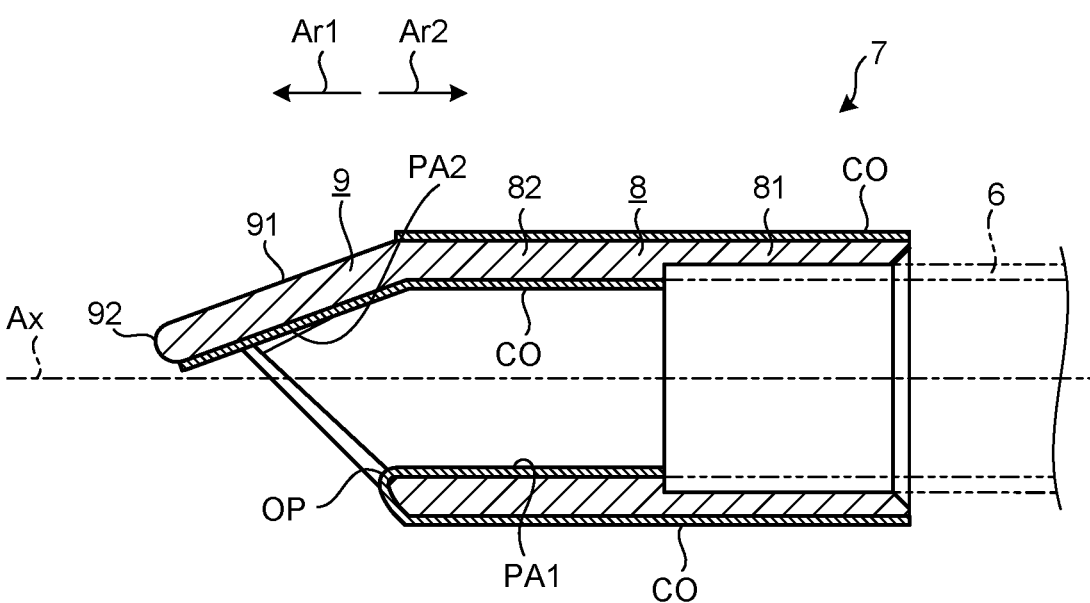
FIG. 5 is a view illustrating an electrode with a conduit.

FIGS. 2 to 5 are views respectively illustrating the conduit electrode 7. Specifically, FIG. 2 is a perspective view of the conduit electrode 7 as viewed from the distal end side Ar1. FIG. 3 is a view of the conduit electrode 7 as viewed from an upper side in FIG. 1. FIG. 4 is a view of the conduit electrode 7 as viewed from a direction perpendicular to a paper surface of FIG. 1. FIG. 5 is a cross-sectional view of the conduit electrode 7 cut along a plane including the central axis Ax. A posture of the conduit electrode 7 illustrated in FIG. 4 is the same as a posture of the conduit electrode 7 illustrated in FIG. 5. For better understanding, a coating layer CO is illustrated only in FIG. 5, not in FIGS. 2 to 4.

As illustrated in FIGS. 2 to 5, the conduit electrode 7 includes a tubular portion 8 and a distal end portion 9.

The tubular portion 8 is a cylindrical member in which a first conduit PA1 is provided to extend linearly along the central axis Ax such that a central axis of the first conduit PA1 coincides with the central axis Ax. An inner surface of the tubular portion 8 has an inner diameter larger on the proximal end side Ar2 than on the distal end side Ar1, and also has a stepped shape. For better understanding, a site on the proximal end side Ar2 having a larger inner diameter is referred to as a proximal end site 81, and a site on the distal end side Ar1 having a smaller inner diameter is referred to as a distal end site 82, in the tubular portion 8.

The conduit electrode 7 is attached to the end portion of the sheath 6 on the distal end side Ar1 by inserting a portion of the sheath 6 on the distal end side Ar1 into the proximal end site 81 (FIG. 5). The conduit electrode 7 may be undetachably fixed to or detachably attached to the end portion of the sheath 6 on the distal end side Ar1.

The distal end portion 9 is a substantially tubular member protruding from a distal end of the tubular portion 8. As illustrated in FIGS. 2 to 5, the distal end portion 9 includes a second conduit PA2 (FIG. 5), an opening OP (FIGS. 2 and 5), and first and second hemostatic surfaces 91 and 92.

As illustrated in FIG. 5, the second conduit PA2 is provided inside the distal end portion 9. The second conduit PA2 extends continuously from the first conduit PA1 linearly along a direction intersecting the central axis Ax.

The opening OP is provided at a distal end of the second conduit PA2, and allows communication between the second conduit PA2 and the outside of the distal end portion 9. That is, the opening OP serves as a suction hole for sucking up body fluid, water, and the like. As illustrated in FIG. 5, the opening OP opens in a direction intersecting the central axis Ax and has an opening area larger than a cross-sectional area of the first conduit PA1.

The first and second hemostatic surfaces 91 and 92 are portions that constitute a part of the outer surface of the distal end portion 9 and function as an electrode that causes a high-frequency current to flow to the hemostasis target site.

Specifically, as illustrated in FIG. 5, the first hemostatic surface 91 is constituted of a flat surface extending from the distal end of the tubular portion 8 in an extending direction of the second conduit PA2. That is, the first hemostatic surface 91 is inclined with respect to the central axis Ax. A part of the first hemostatic surface 91 protrudes toward the distal end side Ar1 from the opening OP.

The second hemostatic surface 92 is an end portion protruding toward the distal end side Ar1 from the opening OP in the distal end portion 9. More specifically, the second hemostatic surface 92 is a surface that is connected to the distal end side Ar1 with respect to the first hemostatic surface 91 and faces a direction different from that of the first hemostatic surface 91. As illustrated in FIG. 3, the second hemostatic surface 92 has an arc shape when viewed from an upper side in FIG. 1. As illustrated in FIG. 4 or 5, the second hemostatic surface 92 has a curved surface shape in which upper and lower ridge portions are rounded in FIGS. 4 and 5.

As illustrated in FIG. 5, the conduit electrode 7 described above is provided with a coating layer CO formed of a resin material such as polyimide, polyether ether ketone (PEEK), or fluororesin having electrical insulation property.

Specifically, as illustrated in FIG. 5, the coating layer CO is provided on an outer surface of the conduit electrode 7 excluding the first and second hemostatic surfaces 91 and 92. The coating layer CO provided on the outer surface of the conduit electrode 7 excluding the first and second hemostatic surfaces 91 and 92 corresponds to a first coating layer. The coating layer CO is provided on an inner surface of the distal end site 82 and an inner surface of the distal end portion 9, among an inner surface of the conduit electrode 7. The coating layer CO provided on the inner surface of the distal end site 82 and the inner surface of the distal end portion 9 corresponds to a second coating layer.

Example of Hemostatic Operation

Next, one example of a hemostatic operation on the hemostasis target site using the treatment tool 1 stated above will be described.

First, in a case where bleeding is observed from a biological tissue, the operator performs the water supply operation for the water supply switch 4 in order to find the hemostasis target site which is a bleeding site. In response to the water supply operation, an external water supply source (not illustrated) connected to the treatment tool 1 by a tube T supplies water. The water is supplied from the opening OP to the biological tissue along a path connecting the tube T, the housing 2, the sheath 6, the first conduit PA1 and the second conduit PA2 in this order. Accordingly, the water is stored on the biological tissue, and the operator finds the hemostasis target site which is a bleeding site.

Next, the operator performs the suction operation for the suction switch (not illustrated). In response to the suction operation, an external suction source (not illustrated) connected to the treatment tool 1 by the tube T is driven. The water stored on the biological tissue runs along a path connecting the opening OP, the second conduit PA2, the first conduit PA1, the sheath 6, the housing 2 and the tube T in this order, and is sucked into the suction source (not illustrated).

Next, the operator performs the hemostasis initiating operation for the hemostasis initiating switch 3 while the first hemostatic surface 91 or the second hemostatic surface 92 is in contact with the hemostasis target site. The conduit electrode 7 is electrically connected to an external control device (not illustrated) via the sheath 6 and a cable C. In response to the hemostasis initiating operation, the control device (not illustrated) supplies high-frequency power between the conduit electrode 7 (the first hemostatic surface 91 or the second hemostatic surface 92) and a counter electrode plate (not illustrated) attached to a surface of a subject. Consequently, a high-frequency current flows through the hemostasis target site located between the first hemostatic surface 91 or the second hemostatic surface 92 and the counter electrode plate (not illustrated). The external water supply source (not illustrated) supplies water in response to the hemostasis initiating operation. An amount of water supplied from the external water supply source (not illustrated) according to the hemostasis initiating operation is smaller than an amount of water supplied from the water supply source according to the water supply operation. Hereinafter, for better understanding, the amount of water supplied from the water supply source according to the water supply operation is referred to as a first amount supplied, and the amount of water supplied from the water supply source according to the hemostasis initiating operation is referred to as a second amount supplied. The water runs along a path connecting the tube T, the housing 2, the sheath 6, the first conduit PA1 and the second conduit PA2 in this order, and drips little by little from the opening OP between the first hemostatic surface 91 or the second hemostatic surface 92 and the hemostasis target site. That is, bleeding at the hemostasis target site is stopped as the high-frequency current flows while water is dripped little by little.

According to the present embodiment described above, the following advantageous effects are achieved.

In the conduit electrode 7 according to the present embodiment, the first conduit PA1 extends along the central axis Ax. On the other hand, the second conduit PA2 extends in the direction intersecting the central axis Ax. The opening OP opens in a direction intersecting the central axis Ax. The opening area of the opening OP is larger than the cross-sectional area of the first conduit PA1.

Therefore, according to the conduit electrode 7 of the present embodiment, it is possible to improve suction efficiency for body fluid or the like for improving convenience.

In the conduit electrode 7 according to the present embodiment, the first hemostatic surface 91 is inclined with respect to the central axis Ax. That is, the conduit electrode 7 has a tapered shape. Therefore, it is easy to recognize, for example, the hemostasis target site located at the back of the conduit electrode 7, and improved visibility can be achieved.

In the conduit electrode 7 according to the present embodiment, the first hemostatic surface 91 is constituted of the flat surface. Therefore, it is possible to stop bleeding at the hemostasis target site in a wide range by means of the first hemostatic surface 91.

In the conduit electrode 7 according to the present embodiment, the second hemostatic surface 92 protrudes toward the distal end side Ar1 from the opening OP and has an annular shape. Therefore, it is easy to bring the second hemostatic surface 92 into contact with the hemostasis target site in a narrow range, and bleeding at the hemostasis target site can be satisfactorily stopped in the narrow range.

In the conduit electrode 7 according to the present embodiment, the coating layer CO is provided on the outer surface excluding the first and second hemostatic surfaces 91 and 92. Therefore, it is possible to prevent the high-frequency current from flowing to a biological tissue other than the hemostasis target site, and to prevent thermal invasion into the other biological tissue.

In the conduit electrode 7 according to the present embodiment, the coating layer CO is provided on the inner surface of the distal end site 82 and the inner surface of the distal end portion 9. Therefore, it is possible to prevent the biological tissue that has entered the inside of the conduit electrode 7 from the opening OP from adhering to the inner surface of the conduit electrode 7.

OTHER EMBODIMENTS

The embodiment for carrying out the disclosure has been described; however, the disclosure is not limited to the embodiment stated above.

Any of Modified Examples 1 to 13, as respectively illustrated in FIGS. 6 to 18, may be adopted in the embodiment stated above.

Modified Example 1

Figure 6:
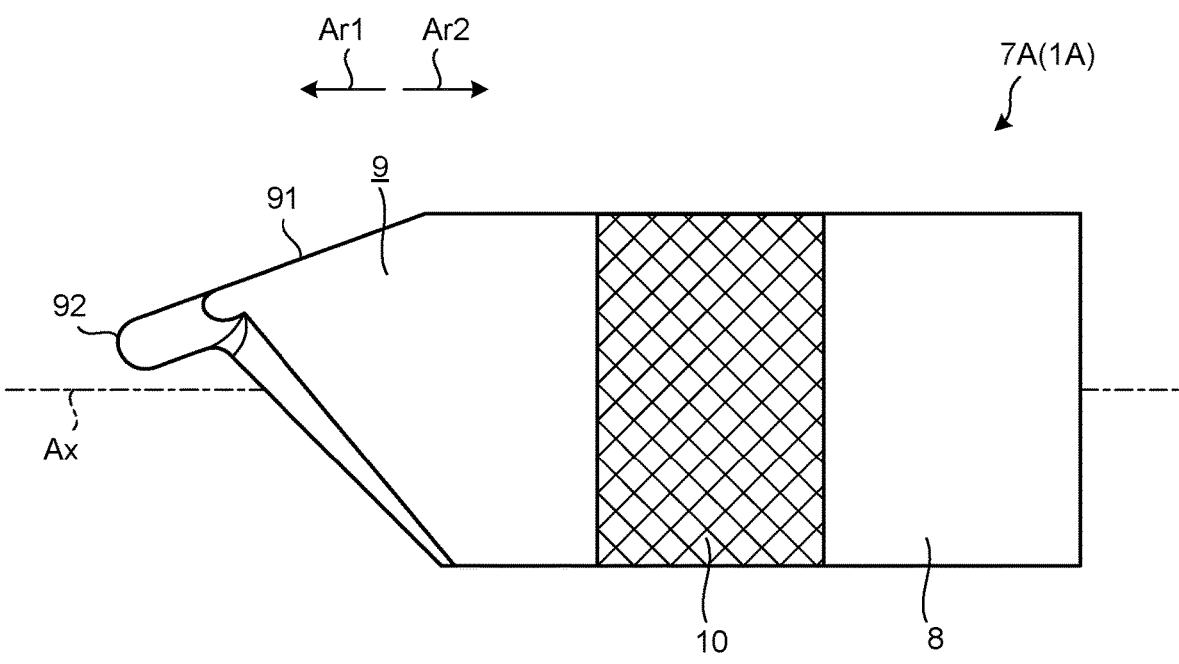
FIG. 6 is a view illustrating Modified Example 1 of an exemplary embodiment.

FIG. 6 is a view illustrating Modified Example 1 of the embodiment. In particular, FIG. 6 is a diagram corresponding to FIG. 4.

A treatment tool 1A (conduit electrode 7A) according to Modified Example 1, as illustrated in FIG. 6, has a permeation site 10 provided in the tubular portion 8. The permeation site 10 has a mesh shape that communicates the inside and outside of the tubular portion 8, and is provided over the entire circumference in a circumferential direction about the central axis Ax. When the hemostasis initiating operation is performed, water is dripped little by little between the first hemostatic surface 91 or the second hemostatic surface 92 and the hemostasis target site by passing through the permeation site 10. Consequently, it is possible to sufficiently suppress adhesion of the biological tissue to the first hemostatic surface 91 or the second hemostatic surface 92.

The permeation site 10 may be provided in the sheath 6 instead of the conduit electrode 7A.

Modified Example 2

Figure 7:
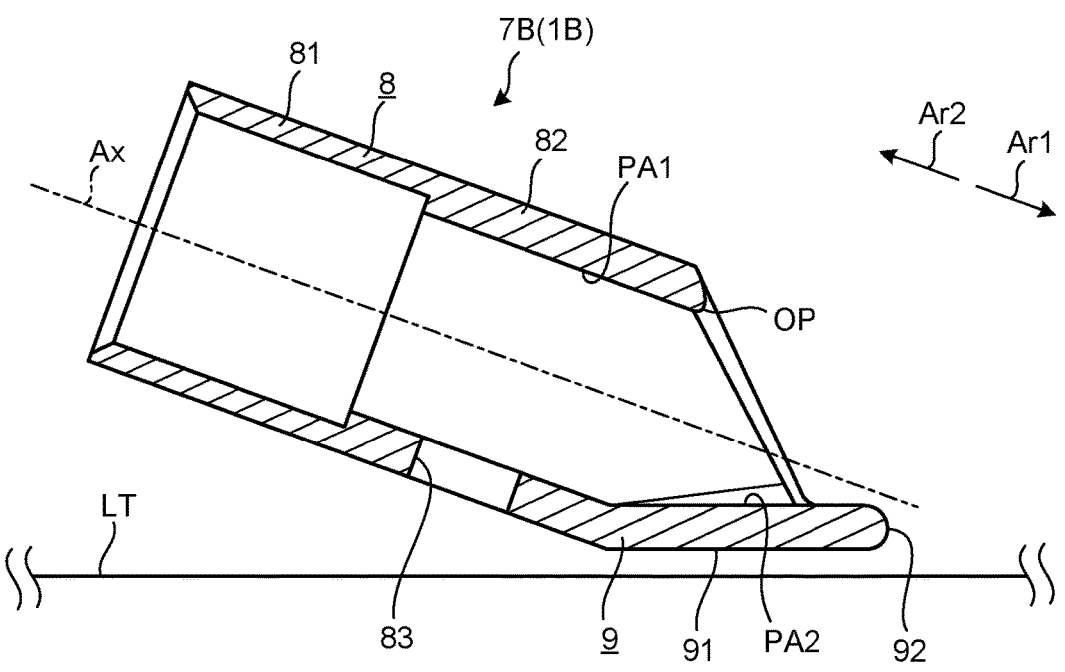
FIG. 7 is a view illustrating Modified Example 2 of an exemplary embodiment.

FIG. 7 is a view illustrating Modified Example 2 of the embodiment. In particular, FIG. 7 is a diagram corresponding to FIG. 5. The coating layer CO is omitted in FIG. 7 for convenience of description.

A treatment tool 1B (conduit electrode 7B) according to Modified Example 2, as illustrated in FIG. 7, has a through hole 83 to prevent a biological tissue LT from being adhered to the tubular portion 8. The through hole 83 is a hole penetrating the inside and outside of the tubular portion 8, and is provided at a position where the first and second hemostatic surfaces 91 and 92 are extended to the proximal end side Ar2 along the central axis Ax. When the hemostasis initiating operation is performed, water is dripped little by little between the first hemostatic surface 91 or the second hemostatic surface 92 and the biological tissue LT (hemostasis target site) by passing through the through hole 83. Consequently, it is possible to sufficiently suppress adhesion of the biological tissue LT to the first hemostatic surface 91 or the second hemostatic surface 92.

Modified Example 3

Figure 8:
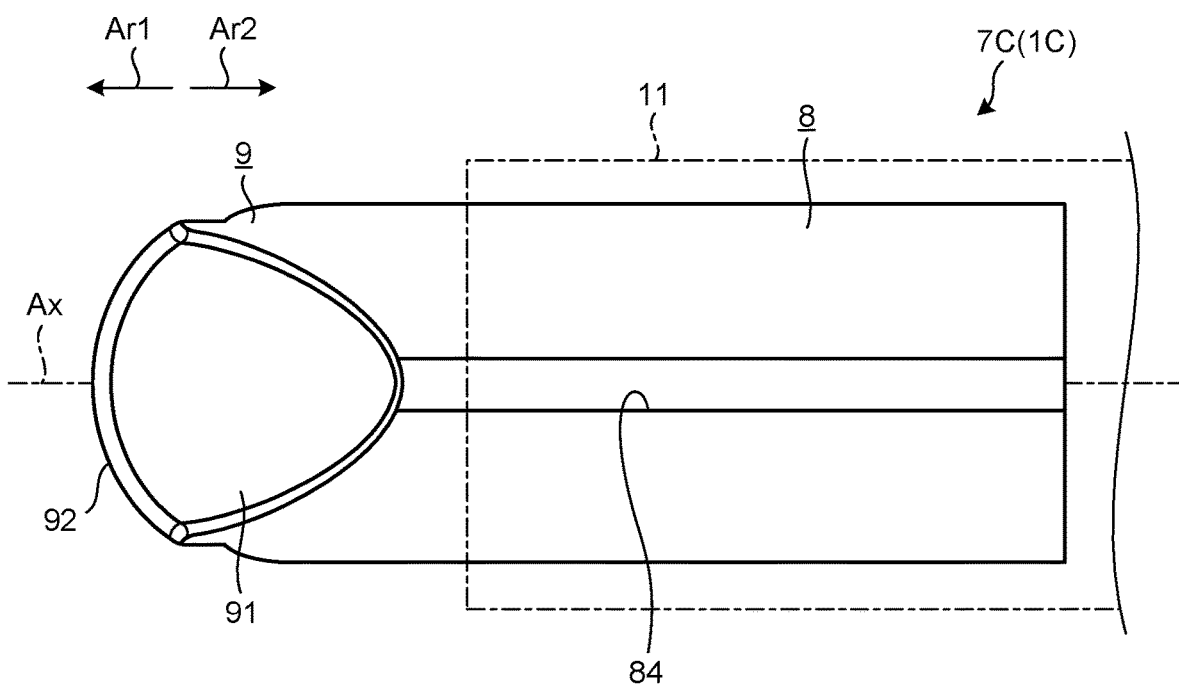
FIG. 8 is a view illustrating Modified Example 3 of an exemplary embodiment.

FIG. 8 is a view illustrating Modified Example 3 of the embodiment. In particular, FIG. 8 is a diagram corresponding to FIG. 3.

A treatment tool 1C (conduit electrode 7C) according to Modified Example 3, as illustrated in FIG. 8, has a groove portion 84 provided on an outer surface of the tubular portion 8. The groove portion 84 is connected to the first hemostatic surface 91, and linearly extends from a position connected to the first hemostatic surface 91 to the proximal end of the conduit electrode 7C along the central axis Ax. Although not specifically illustrated, the outer surface of the sheath 6 is also provided with a groove portion communicating with the groove portion 84 and extending from the distal end to the proximal end of the sheath 6. An opening of the groove portion 84 and an opening of the groove portion (not illustrated) of the sheath 6 are closed by the tube 11. When the hemostasis initiating operation is performed, water is dripped little by little between the first hemostatic surface 91 or the second hemostatic surface 92 and the hemostasis target site by passing through the groove portion (not illustrated) of the sheath 6 and the groove portion 84. Consequently, it is possible to sufficiently suppress adhesion of the biological tissue to the first hemostatic surface 91 or the second hemostatic surface 92. Since a line, i.e. the groove portion (not illustrated) of the sheath 6 and the groove portion 84, through which water is dripped is provided separately from a line, e.g. first and second conduits PA1 and PA2, through which water is supplied and sucked, the line through which water is dripped is not emptied by suction; water can be always filled. Therefore, it is possible to promptly drip water between the first hemostatic surface 91 or the second hemostatic surface 92 and the hemostasis target site.

Modified Example 4

Figure 9:
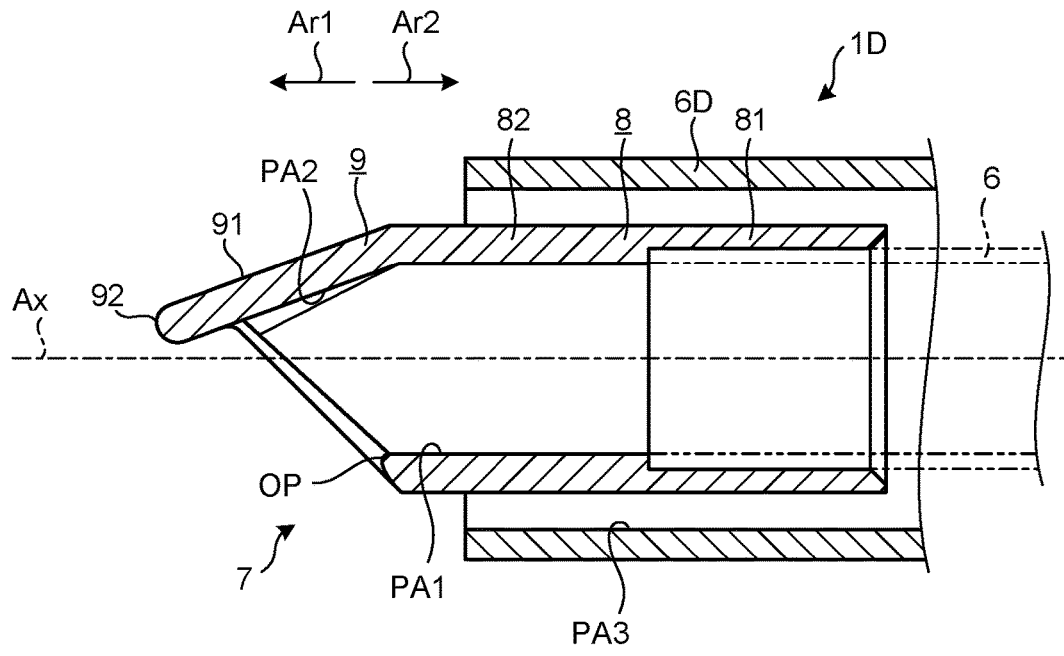
FIG. 9 is a view illustrating Modified Example 4 of an exemplary embodiment.

FIG. 9 is a view illustrating Modified Example 4 of the embodiment. In particular, FIG. 9 is a diagram corresponding to FIG. 5. The coating layer CO is omitted in FIG. 9 for convenience of description.

A treatment tool 1D according to Modified Example 4, as illustrated in FIG. 9, has a second tubular sheath 6D provided to cover the sheath 6 and the tubular portion 8. Consequently, a third conduit PA3 is provided between an inner surface of the second sheath 6D, and the outer surface of the sheath 6 and the outer surface of the tubular portion 8. When the hemostasis initiating operation is performed, water is dripped little by little between the first hemostatic surface 91 or the second hemostatic surface 92 and the hemostasis target site by passing through the third conduit PA3. Consequently, it is possible to sufficiently suppress adhesion of the biological tissue to the first hemostatic surface 91 or the second hemostatic surface 92.

Modified Example 5

Figure 10:
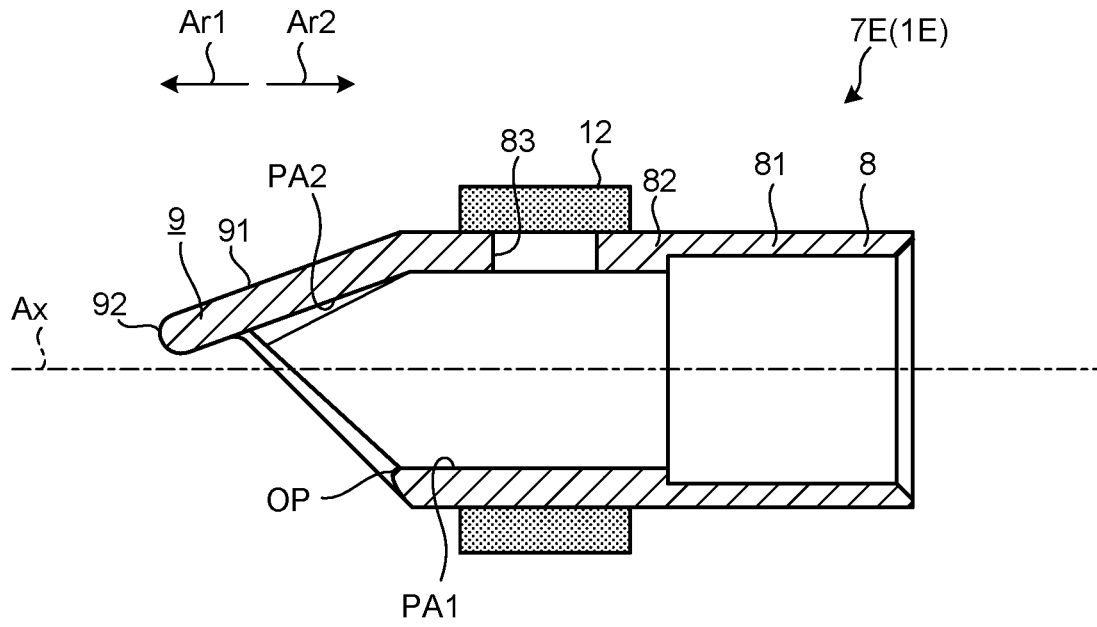
FIG. 10 is a view illustrating Modified Example 5 of the embodiment.

FIG. 10 is a view illustrating Modified Example 5 of the embodiment. In particular, FIG. 10 is a diagram corresponding to FIG. 5. The coating layer CO is omitted in FIG. 10 for convenience of description.

A treatment tool 1E (conduit electrode 7E) according to Modified Example 5, has a sponge ring 12 provided with respect to the conduit electrode 7B (FIG. 7) according to Modified Example 2 stated above. The sponge ring 12 is formed of a porous member capable of holding liquid, has an annular shape about the central axis Ax, and is attached to the outer surface of the tubular portion 8 so as to close the through hole 83. Water discharged to the outside via the through hole 83 in response to the water supply operation or the hemostasis initiating operation is held by the sponge ring 12. The water held by the sponge ring 12 is dripped little by little between the first hemostatic surface 91 or the second hemostatic surface 92 and the hemostasis target site by sandwiching the sponge ring 12 between the first hemostatic surface 91 or the second hemostatic surface 92 and the hemostasis target site when the operator attempts to stop bleeding at the hemostasis target site. Consequently, it is possible to sufficiently suppress adhesion of the biological tissue to the first hemostatic surface 91 or the second hemostatic surface 92. It is possible to promptly drip water between the first hemostatic surface 91 or the second hemostatic surface 92 and the hemostasis target site.

In Modified Examples 1 to 5 stated above, a structure for suppressing adhesion of the biological tissue to the first hemostatic surface 91 or the second hemostatic surface 92 has been described, but such a structure is not limited thereto.

For example, in the embodiment as stated above, water may be stored on a back surface of the first hemostatic surface 91 in the distal end portion 9 while the first hemostatic surface 91 faces downward, and such water may be dripped to the hemostasis target site when the operator attempts to stop bleeding at the hemostasis target site. In this way, similarly to Modified Example 5 stated above, it is possible to promptly drip water between the first hemostatic surface 91 or the second hemostatic surface 92 and the hemostasis target site.

For example, the first hemostatic surface 91 and the second hemostatic surface 92 may be made of carbon which is a material to which the biological tissue is hardly adhered.

Furthermore, for example, the first hemostatic surface 91 and the second hemostatic surface 92 may have an uneven shape to which the biological tissue is hardly adhered.

For example, the first hemostatic surface 91 may be configured to have a curved surface to which the biological tissue is hardly adhered.

In a case where there is no water between the first hemostatic surface 91 or the second hemostatic surface 92 and the hemostasis target site, the biological tissue is easily adhered to the first hemostatic surface 91 or the second hemostatic surface 92. Therefore, a structure may be adopted in which a sensor for detecting water is provided, and the high-frequency current flows to the hemostasis target site only when the water is detected.

In Modified Example 5 stated above, an osmosis membrane may be adopted instead of the sponge ring 12. Water discharged to the outside via the through hole 83 in response to the water supply operation or the hemostasis initiating operation is held by the osmosis membrane. When the operator attempts to stop bleeding at the hemostasis target site, the osmosis membrane is brought into contact with blood or the like to drip the held water little by little between the first hemostatic surface 91 or the second hemostatic surface 92 and the hemostasis target site.

Modified Example 6

Figure 11:
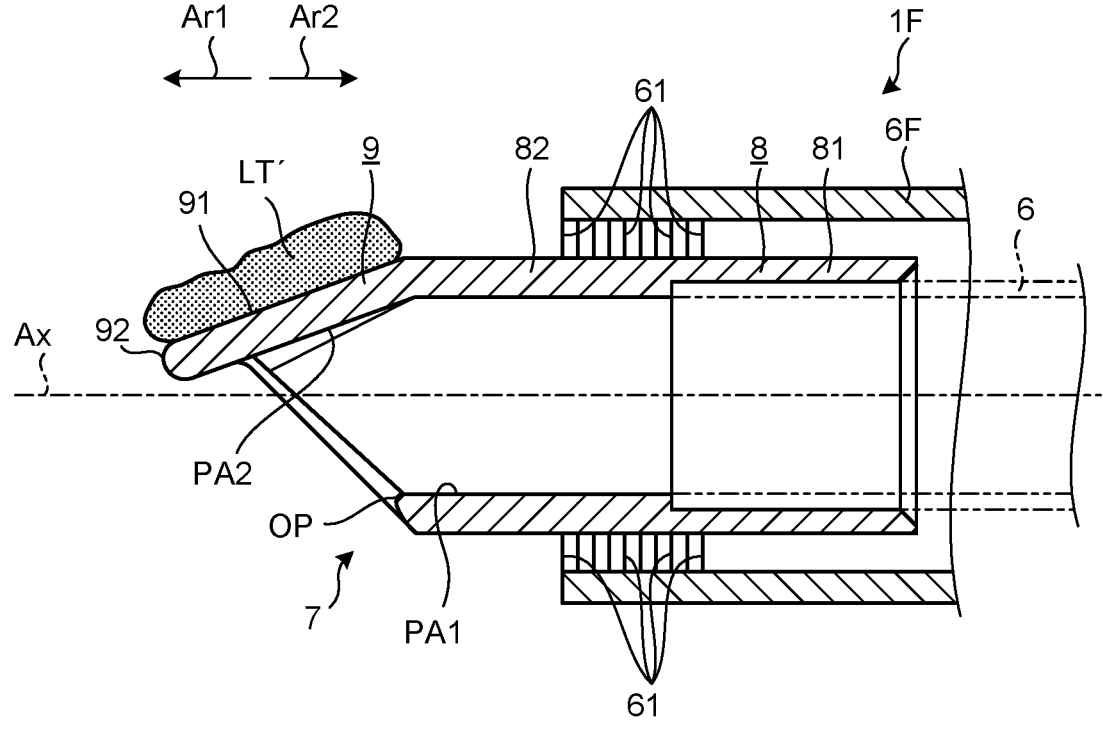
FIG. 11 is a view illustrating Modified Example 6 of an exemplary embodiment.

FIG. 11 is a view illustrating Modified Example 6 of the embodiment. In particular, FIG. 11 is a diagram corresponding to FIG. 5. The coating layer CO is omitted in FIG. 11 for convenience of description.

A treatment tool 1F according to Modified Example 6, as illustrated in FIG. 11, has a second tubular sheath 6F provided to cover the sheath 6 and the tubular portion 8. In the second sheath 6F, a plurality of brush bristles 61 are implanted on the distal end side Ar1 of the inner surface. Further, the second sheath 6F is provided to be movable forward and backward along the central axis Ax with respect to the sheath 6 and the tubular portion 8. When the biological tissue LT' adheres to the first hemostatic surface 91 or the second hemostatic surface 92, the second sheath 6F is moved forward and backward. Consequently, the biological tissue LT' is peeled off from the first hemostatic surface 91 or the second hemostatic surface 92 by the brush bristles 61.

A structure in which the plurality of brush bristles 61 are omitted may be adopted. In this case, the biological tissue LT' is peeled off from the first hemostatic surface 91 or the second hemostatic surface 92 by the second sheath 6F itself. Additionally, the second sheath 6F may be configured to be movable forward and backward along the central axis Ax, or be rotatable along a circumferential direction about the central axis Ax.

In Modified Example 6 stated above, a structure for peeling off the adhered biological tissue LT' from the first hemostatic surface 91 or the second hemostatic surface 92 has been described, but such a structure is not limited thereto.

For example, a device such as another treatment tool may be provided with a site having large friction, and the biological tissue LT' may be peeled off by rubbing the first hemostatic surface 91 or the second hemostatic surface 92 against the site.

Furthermore, for example, the biological tissue LT' may be peeled off by ejecting water having a high flow rate from the through hole 83 toward the first hemostatic surface 91 or the second hemostatic surface 92 while the opening OP is blocked by another member (e.g. the biological tissue or the like) in Modified Example 2 stated above.

Furthermore, for example, the biological tissue LT' may be peeled off by ejecting water having a high flow rate from the third conduit PA3 toward the first hemostatic surface 91 or the second hemostatic surface 92 in Modified Example 4.

Modified Example 7

Figure 12:
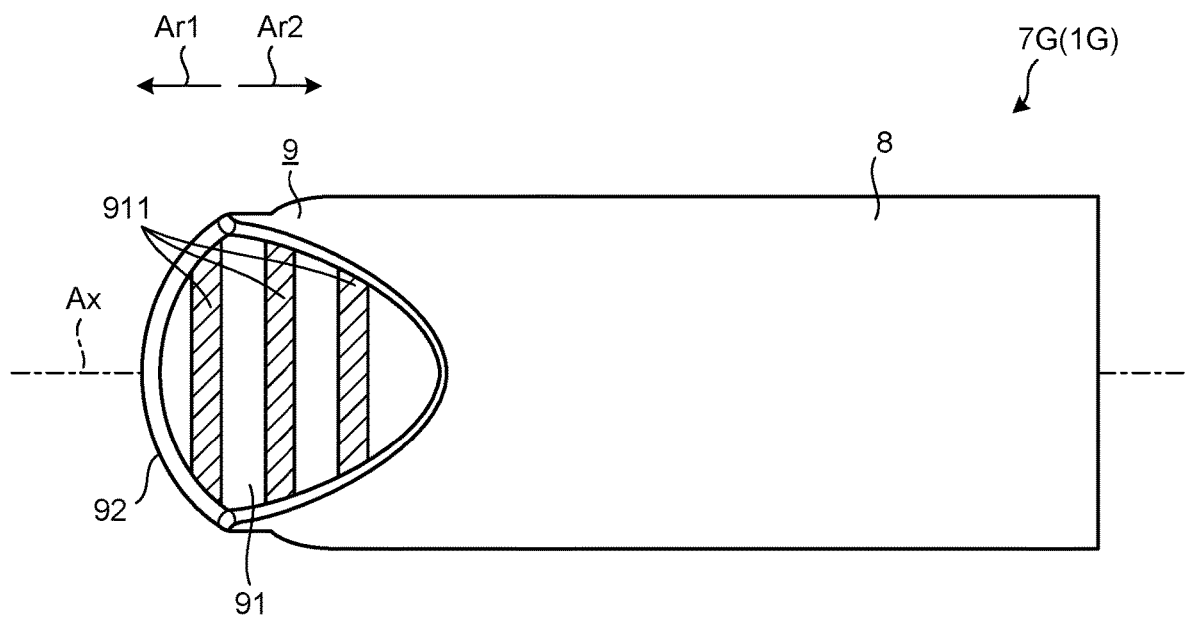
FIG. 12 is a view illustrating Modified Example 7 of an exemplary embodiment.

FIG. 12 is a view illustrating Modified Example 7 of the embodiment. In particular, FIG. 12 is a diagram corresponding to FIG. 3.

A treatment tool 1G (conduit electrode 7G) according to Modified Example 7, as illustrated in FIG. 12, has an insulation member 911 provided at a part of the first hemostatic surface 91. The insulation member 911 is made of the same material as the coating layer CO. That is, an area where the biological tissue adheres to the first hemostatic surface 91 is reduced by providing the insulation member 911 at a part of the first hemostatic surface 91, and thus the biological tissue adhering to the first hemostatic surface 91 can be easily peeled off.

In FIG. 12, the insulation member 911 is provided on the first hemostatic surface 91 only, but the disclosure is not limited thereto; the insulation member 911 may also be provided at a part of the second hemostatic surface 92.

In Modified Example 7 stated above, a structure for easily peeling off the adhered biological tissue from the first hemostatic surface 91 or the second hemostatic surface 92 has been described, but such a structure is not limited thereto.

For example, a heater is provided for the conduit electrode 7. The biological tissue adhered to the first hemostatic surface 91 or the second hemostatic surface 92 is carbonized by heat generated from the heater. Consequently, the biological tissue is easily peeled off.

Modified Example 8

Figure 13:
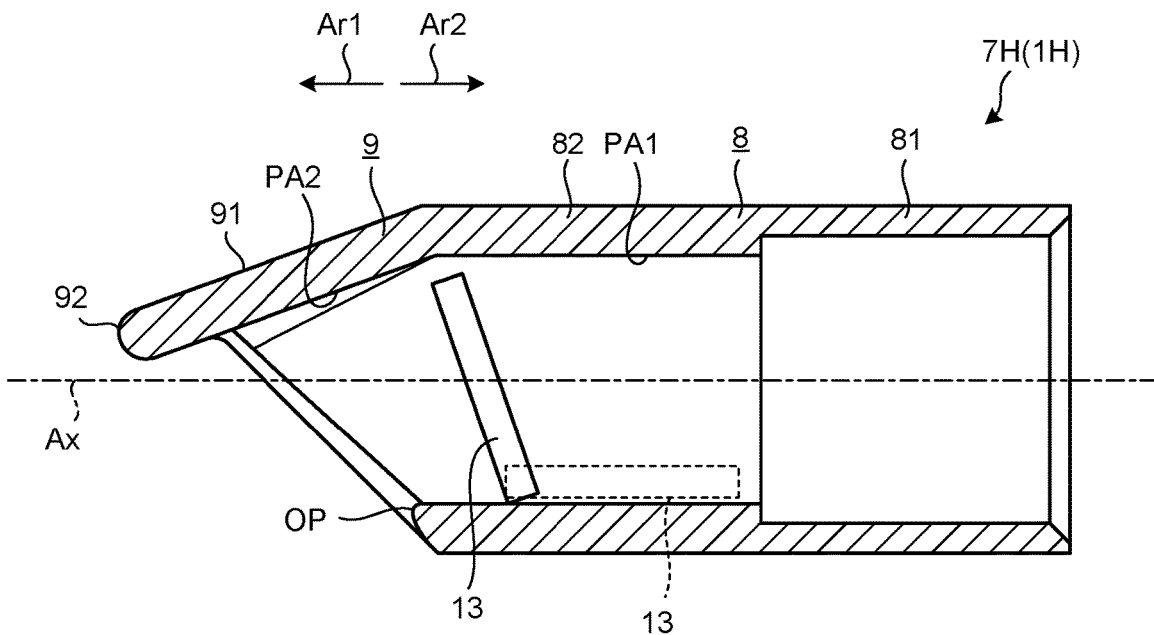
FIG. 13 is a view illustrating Modified Example 8 of an exemplary embodiment.

FIG. 13 is a view illustrating Modified Example 8 of the embodiment. In particular, FIG. 13 is a diagram corresponding to FIG. 5. The coating layer CO is omitted in FIG. 13 for convenience of description.

A treatment tool 1H (conduit electrode 7H) according to Modified Example 8, as illustrated in FIG. 13, has a valve 13 provided in the tubular portion 8. The valve 13 opens the first conduit PA1 as indicated by a broken line in FIG. 13 in a normal state where the hemostasis initiating operation is not performed. When only the water supply operation is performed, water is supplied from the opening OP toward the biological tissue in the first amount supplied through the opened first conduit PA1. Meanwhile, the valve 13 partially closes the first conduit PA1 as indicated by a solid line in FIG. 13 when the hemostasis initiating operation is performed. When the hemostasis initiating operation and the water supply operation are simultaneously performed, water is supplied to the first conduit PA1 in the first amount supplied. However, since the first conduit PA1 is partially blocked by the valve 13, water is dripped from the opening OP to between the first hemostatic surface 91 or the second hemostatic surface 92 and the hemostasis target site in the second amount supplied, via a gap between the valve 13 and the first conduit PA1. That is, as compared with a configuration in which water is supplied with the second amount supplied to the first conduit PA1, water can be promptly dripped between the first hemostatic surface 91 or the second hemostatic surface 92 and the hemostasis target site.

Modified Example 9

Figure 14:
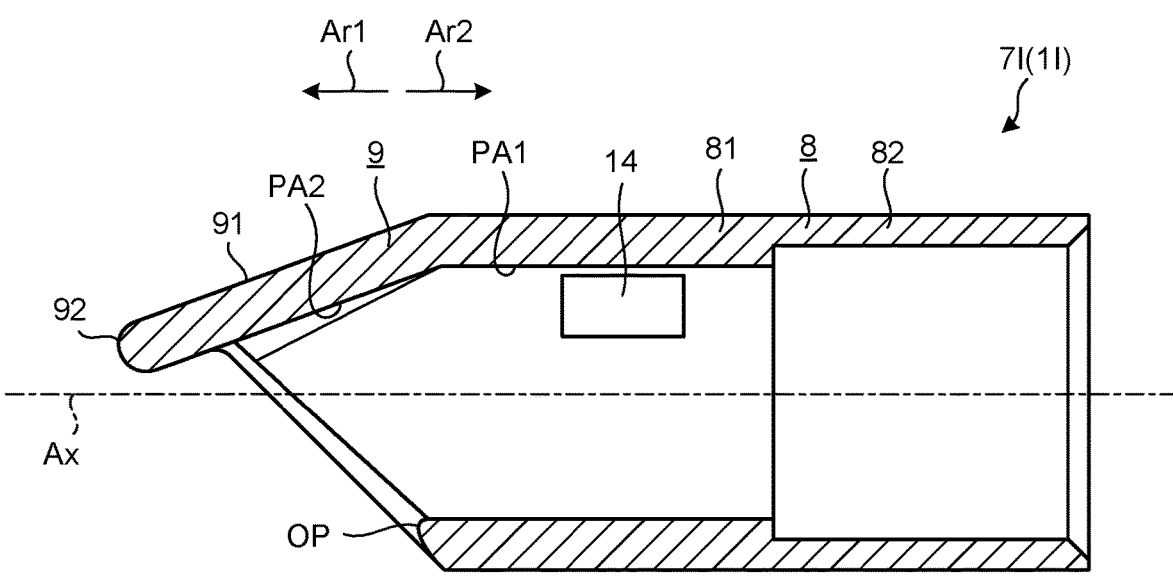
FIG. 14 is a view illustrating Modified Example 9 of an exemplary embodiment.

FIG. 14 is a view illustrating Modified Example 9 of the embodiment. In particular, FIG. 14 is a diagram corresponding to FIG. 5. The coating layer CO is omitted in FIG. 14 for convenience of description.

A treatment tool 1I (conduit electrode 7I) according to Modified Example 9, as illustrated in FIG. 14, has a sensor 14 provided in the tubular portion 8. The sensor 14 is a sensor that measures a flow rate of water. In a case where the hemostasis initiating operation is performed, the external water supply source (not illustrated) supplies water to the first conduit PA1 in the first amount supplied. In a case where the sensor 14 detects that the flow rate of the water is equivalent to the first amount supplied, the water supply source switches the amount of water supplied to the second amount supplied. Consequently, water is dripped from the opening OP to between the first hemostatic surface 91 or the second hemostatic surface 92 and the hemostasis target site in the second amount supplied. That is, as compared with a configuration in which water is supplied with the second amount supplied to the first conduit PA1 in response to the hemostasis initiating operation, water can be promptly dripped between the first hemostatic surface 91 or the second hemostatic surface 92 and the hemostasis target site.

In Modified Examples 8 and 9 stated above, a configuration in which water is promptly dripped between the first hemostatic surface 91 or the second hemostatic surface 92 and the hemostasis target site has been described, but such a configuration is not limited thereto.

For example, an acceleration pump using water or air is provided inside the housing 2. In response to the hemostasis initiating operation, the acceleration pump is driven to apply pressure to water supplied in the second amount supplied from the external water supply source (not illustrated) by the acceleration pump, and the water is supplied to the first conduit PA1 in an amount supplied larger than the second amount supplied. The driving of the acceleration pump is then stopped. Consequently, water is dripped from the opening OP to between the first hemostatic surface 91 or the second hemostatic surface 92 and the hemostasis target site in the second amount supplied. That is, as compared with a configuration of the embodiment stated above, in which the acceleration pump is not introduced, water can be promptly dripped between the first hemostatic surface 91 or the second hemostatic surface 92 and the hemostasis target site.

For example, the hemostasis initiating switch 3 is configured as a button that can be pushed in two steps. In a case where the hemostasis initiating switch 3 is pushed in a first step, the external water supply source (not illustrated) supplies water to the first conduit PA1 in an amount supplied larger than the second amount supplied. In a case where the hemostasis initiating switch 3 is pushed in a second step, the water supply source supplies water to the first conduit PA1 in the second amount supplied. Consequently, water is dripped from the opening OP to between the first hemostatic surface 91 or the second hemostatic surface 92 and the hemostasis target site in the second amount supplied. That is, as compared with a configuration in which water is supplied with the second amount supplied to the first conduit PA1 in response to the hemostasis initiating operation, water can be promptly dripped between the first hemostatic surface 91 or the second hemostatic surface 92 and the hemostasis target site.

In Modified Example 9, the external water supply source (not illustrated) switches the amount of water supplied from the first amount supplied to the second amount supplied in a case where the sensor 14 detects that the flow rate of the water is equivalent to the first amount supplied; however the disclosure is not limited thereto. For example, a configuration may be adopted in which the amount of water supplied is switched to the second amount supplied when a specific time has been elapsed after the water is supplied in the first amount supplied.

Modified Example 10

Figure 15:
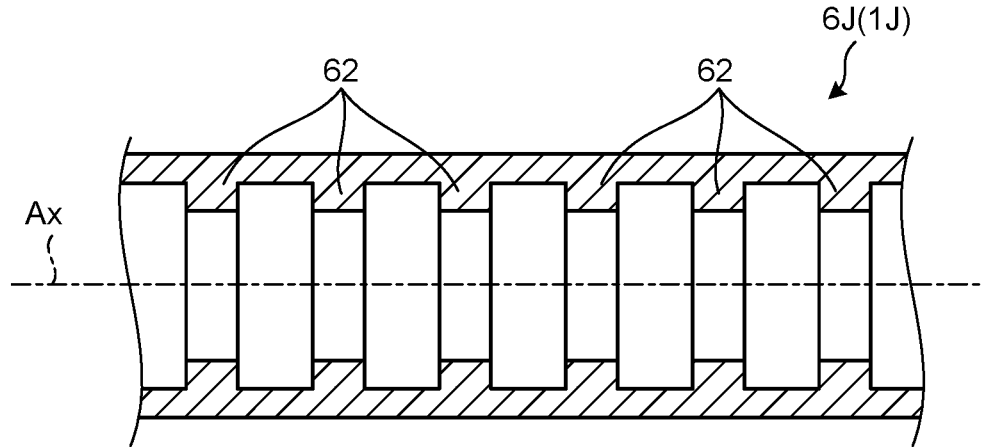
FIG. 15 is a view illustrating Modified Example 10 of an exemplary embodiment.

FIG. 15 is a view illustrating Modified Example 10 of the embodiment.

A treatment tool 1J according to Modified Example 10, annular protrusions 62 are provided at regular intervals inside a sheath 6J. That is, the inside of the sheath 6J has a structure imitating the neck of a giraffe. Consequently, a flow path resistance of water flowing inside of the sheath 6J decreases, while increasing a flow rate, as compared with a configuration without the protrusions 62. Therefore, it is possible to promptly drip water between the first hemostatic surface 91 or the second hemostatic surface 92 and the hemostasis target site.

Modified Example 11

Figure 16:
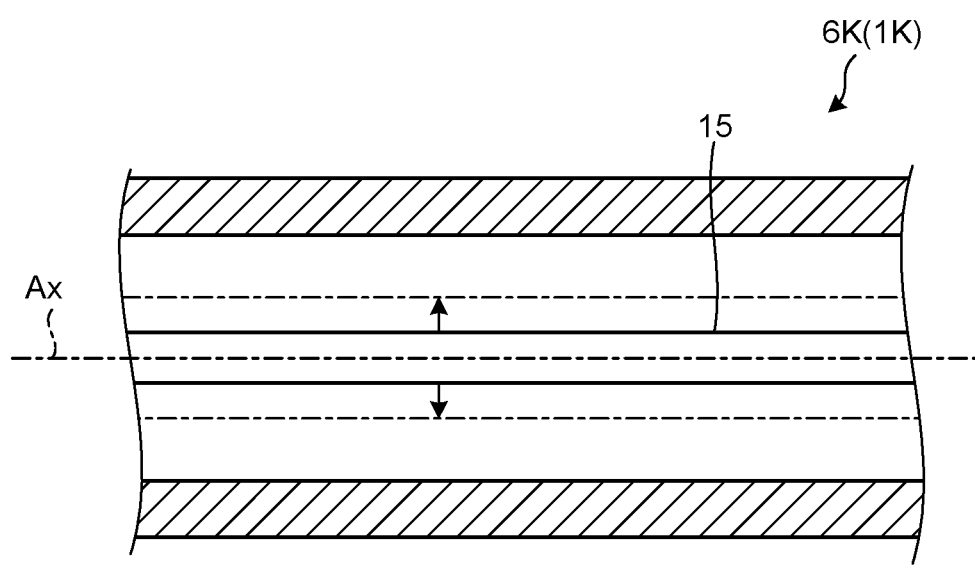
FIG. 16 is a view illustrating Modified Example 11 of an exemplary embodiment.

FIG. 16 is a view illustrating Modified Example 11 of the embodiment.

A treatment tool 1K according to Modified Example 11 has a balloon 15 that is provided inside a sheath 6K. The balloon 15 may be inflated as indicated by a broken line in FIG. 16 or deflated as indicated by a solid line in FIG. 16 to adjust a flow rate of water flowing inside of the sheath 6K. Therefore, it is possible to promptly drip water between the first hemostatic surface 91 or the second hemostatic surface 92 and the hemostasis target site.

Modified Example 12

Figure 17:
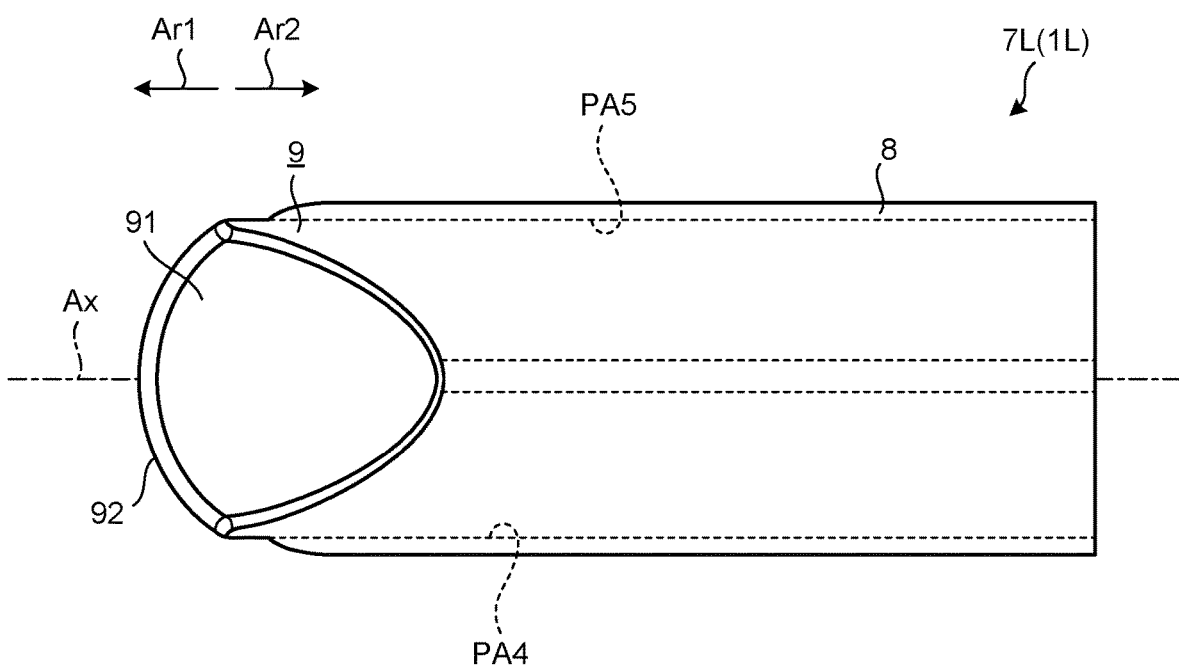
FIG. 17 is a view illustrating Modified Example 12 of an exemplary embodiment.

FIG. 17 is a view illustrating Modified Example 12 of the embodiment. In particular, FIG. 17 is a diagram corresponding to FIG. 3.

In a treatment tool 1L (conduit electrode 7L) according to Modified Example 12, as illustrated in FIG. 17, the first and second conduits PA1 and PA2 are replaced by fourth and fifth conduits PA4 and PA5. The fourth and fifth conduits PA4 and PA5 are independent from each other, and extend along the central axis Ax. Although not specifically illustrated, the sheath 6 is also provided with conduits respectively communicating with the fourth and fifth conduits PA4 and PA5, and extending from the distal end to the proximal end of the sheath 6. The fourth conduit PA4 is a line for supplying water according to the water supply operation and dripping water according to the hemostasis initiating operation. On the other hand, the fifth conduit PA5 is a line for sucking up body fluid or the like according to the suction operation. Since a line, i.e. the fourth conduit PA4, through which water is supplied and dripped is provided separately from a line, i.e. the fifth conduit PA5, through which water is sucked up, the fourth conduit PA4 is not emptied by suction; water can be always filled. Therefore, it is possible to promptly drip water between the first hemostatic surface 91 or the second hemostatic surface 92 and the hemostasis target site.

Although the fourth conduit PA4 is the line for supplying water and dripping water, the disclosure is not limited thereto, and the fourth conduit PA4 may be a line for dripping water while the fifth conduit PA5 may be a line for supplying and sucking water.

In addition, the fourth and fifth conduits PA4 and PA5 extend to the distal end of the conduit electrode 7L, but the disclosure is not limited thereto; a structure (Y-shaped branch conduit) may be adopted in which the fourth and fifth conduits PA4 and PA5 is extended to the proximal end side of the distal end of the conduit electrode 7L, and one conduit is extended to the distal end of the conduit electrode 7L from the proximal end side of the distal end of the conduit electrode 7L. At this time, a valve may be provided at a branch at which the fourth and fifth conduits PA4 and PA5 communicate with each other; closing the fifth conduit PA5 in a case where water is supplied and dripped, and closing the fourth conduit PA4 in a case where suction is performed.

Modified Example 13

Figure 18:
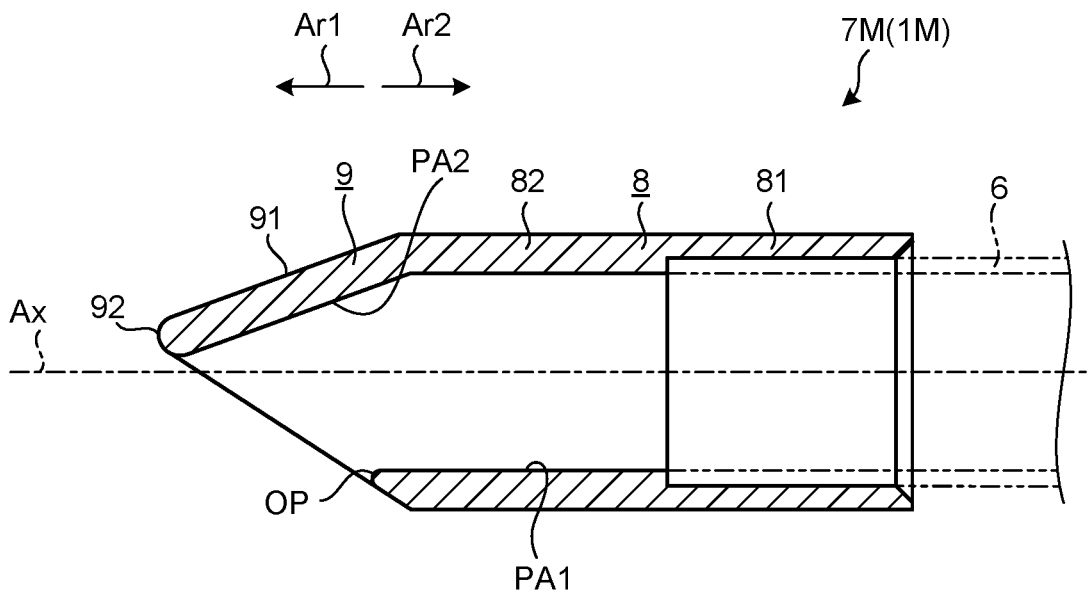
FIG. 18 is a view illustrating Modified Example 13 of an exemplary embodiment.

FIG. 18 is a view illustrating Modified Example 13 of the embodiment. In particular, FIG. 18 is a diagram corresponding to FIG. 5. The coating layer CO is omitted in FIG. 18 for convenience of description.

In the treatment tool 1M (conduit electrode 7M) according to Modified Example 13, a part of the first hemostatic surface 91 and the second hemostatic surface 92 do not protrude toward the distal end side Ar1 from the opening OP in the distal end portion 9.

According to the electrode with a conduit and the treatment tool of the disclosure, it is possible to improve convenience.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An electrode comprising:
a tubular portion that includes a first conduit extending along a longitudinal axis;
a distal end portion including:
  a second conduit extending along a direction intersecting the longitudinal axis, the second conduit communicating with the first conduit;
  an opening in communication with a distal end of the second conduit;
wherein the distal end portion includes:
  a first surface configured to supply energy;
  a second surface configured to supply the energy, the second surface provided distally relative to the first surface, the second surface including a distal edge having an arc shape and a planar surface extending towards the longitudinal axis; and
  a proximal end of a proximal side of the first surface along the longitudinal axis has a larger inner diameter than an inner diameter at a distal portion the tubular portion.
2. The electrode according to claim 1, wherein the second surface faces a direction different from a direction of the first surface faces, the second surface extending obliquely relative to the first surface.

3. The electrode according to claim 1, wherein the second surface has an arc shape.
4. The electrode according to claim 1, wherein an outer surface of the electrode with the conduit, excluding the first surface and the second surface, is provided with a first coating layer having electrical insulation property.
5. The electrode according to claim 1, wherein at least a part of an inner surface of the electrode with the conduit, is provided with a second coating layer having electrical insulation property.
6. The electrode according to claim 1, wherein the tubular portion is provided with a through hole configured to penetrate through the tubular portion and prevent biological tissue from being adhered to the tubular portion.
7. The electrode according to claim 6, wherein the through hole is provided at a proximal side of the first surface along the longitudinal axis.
8. The electrode according to claim 7, wherein the proximal end is located proximally relative to the through hole.
9. The electrode according to claim 1, wherein a diameter of the opening is larger than a diameter of a cross-section of the first conduit.
10. A treatment tool comprising:
a tubular sheath; and
an electrode according to claim 1, the electrode being provided at a distal end of the sheath.
11. The electrode according to claim 1, wherein the opening is provided at a distal end of the second conduit.
12. The electrode according to claim 1, wherein a part of the first surface protrudes toward a distal end side from the opening.
13. The electrode according to claim 1, wherein the second surface includes a curved surface that contacts a rounded ridge portion.
14. The electrode according to claim 1, wherein:
a surface of the opening extends in a direction that intersects with a direction of the first surface, and
the first surface intersects with an opening plane of the opening.
15. The electrode according to claim 1, wherein an end portion of the second surface forms one side of the opening.
16. The electrode according to claim 1, wherein the opening is configured to open in a direction intersecting the longitudinal axis,
the first surface is a flat surface, and
the second surface is provided at distal-most end of the first surface.
17. The electrode according to claim 1, wherein the second surface extends continuously from the first surface in the longitudinal axis.
18. The electrode according to claim 1, wherein the first surface has a curved distal edge portion and a curved proximal edge portion.
19. The electrode according to claim 18, further comprising a first insulating surface on an outer surface of the tubular portion such that form the curved proximal edge portion, excluding the first surface and the second surface, wherein the first insulating surface has electrical insulation property.
20. The electrode according to claim 19, further comprising a second insulating surface on at least a part of an inner surface of the first and the second conduit wherein the second insulating surface has electrical insulation property.
21. The electrode according to claim 1, wherein:
the distal end portion is provided distally relative to the tubular portion, the distal end portion has a substantially cylindrical shape protruding from the distal end of the tubular portion, a portion of an outer surface of the distal end portion is configured to supply a high-frequency current, the first surface is a first hemostatic surface extending along a direction intersecting the longitudinal axis, and the second surface is a second hemostatic surface.

22. The electrode according to claim 1, wherein the tubular portion has a stepped shape.

\* \* \* \* \*